US012748094B2

(12) United States Patent
Tang et al.

(10) Patent No.: US 12,748,094 B2
(45) Date of Patent: Sep. 29, 2026

(54) DEVICE AND METHOD FOR REAL-TIME MONITORING OF WATER CONSUMPTION OF PLANTS IN SALINE-ALKALI LAND

(71) Applicant: Northwest Institute of Eco-Environment and Resources, Chinese Academy of Sciences, Lanzhou City (CN)

(72) Inventors: Xia Tang, Lanzhou City (CN); Hao Qu, Lanzhou City (CN)

(73) Assignee: Northwest Institute of Eco-Environment and Resources, Chinese Academy of Sciences, Lanzhou City (CN)

( * ) Notice: Subject to any disclaimer, the term of this patent is extended or adjusted under 35 U.S.C. 154(b) by 0 days.

(21) Appl. No.: 19/194,870

(22) Filed: Apr. 30, 2025

(65) Prior Publication Data

US 2026/0194509 A1 Jul. 9, 2026

(30) Foreign Application Priority Data

Jan. 7, 2025 (CN) ......................... 202510021142.4

(51) Int. Cl.

*G01N 33/18* (2006.01)
*A01G 25/16* (2006.01)
*G01N 33/00* (2006.01)

(52) U.S. Cl.

CPC ......... *G01N 33/1886* (2013.01); *A01G 25/16* (2013.01); *G01N 33/0098* (2013.01)

(58) Field of Classification Search

CPC .... A01G 22/00; A01G 17/005; A01G 25/167; A01G 25/02; A01G 25/00; A01G 25/16;

(Continued)

(56) References Cited

U.S. PATENT DOCUMENTS 4,866,880 A * 9/1989 Weinblatt ............... A01G 29/00 222/650
5,601,236 A * 2/1997 Wold ..................... A01G 29/00 239/69

(Continued)

FOREIGN PATENT DOCUMENTS

CN 107223505 A * 10/2017 ........... A01G 17/005
CN 213240148 U * 5/2021

(Continued)

OTHER PUBLICATIONS

The China National Intellectual Property Administration, Notification to Grant Patent Right for Invention of priority application 202510021142.4, Sep. 1, 2025, 1 page.

*Primary Examiner* — Andre J Allen
(74) *Attorney, Agent, or Firm* — J. Peter Paredes; Amin Wasserman Gurnani LLP

(57) ABSTRACT

Provided are a device and a method for real-time monitoring of the water consumption of plants in saline-alkali land. The device includes monitoring component, adjusting component and stabilizing component. The monitoring component includes rod body, and the top part of the rod body is provided with control head. The adjusting component is provided at the bottom part of the rod body and includes adjusting member. The adjusting member includes fixing sleeve. The fixing sleeve is fixed at the bottom part of the rod body, guiding sleeve is provided on the outer side of the fixing sleeve, and supporting frame is provided inside of the fixing sleeve. Rotating column is rotatably connected with the interior of the guiding sleeve through bearing, fixing shaft is fixed inside the supporting frame, spiral groove is provided on the rotating column, and the fixing shaft is slidably arranged in the spiral groove.

10 Claims, 8 Drawing Sheets

(58) Field of Classification Search

CPC . A01G 7/06; A01G 20/00; A01G 9/02; A01G 22/22; A01G 22/40; A01G 24/10; A01G 25/06; A01G 31/02; A01G 22/20; A01G 9/14; A01G 31/00; A01G 24/20; A01G 9/247; A01G 24/12; A01G 7/00; A01G 24/00; A01G 11/00; A01G 24/28; A01G 7/045; A01G 13/33; A01G 24/15; A01G 17/00; A01G 18/20; A01G 22/60; A01G 25/09; A01G 18/00; A01G 18/10; A01G 2/10; A01G 25/023; A01G 31/06; A01G 33/00; A01G 9/24; A01G 13/00; A01G 2/00; A01G 24/22; A01G 27/003; A01G 29/00; A01G 9/246; A01G 22/50; A01G 9/023; A01G 9/029; A01G 2/30; A01G 22/15; A01G 24/17; A01G 27/02; A01G 7/02; A01G 9/022; A01G 9/0295; A01G 9/16; A01G 9/18; A01G 9/245; A01G 13/06; A01G 13/35; A01G 2/20; A01G 22/25; A01G 22/35; A01G 23/00; A01G 23/04; A01G 23/043; A01G 24/23; A01G 24/25; A01G 24/30; A01G 24/46; A01G 25/092; A01G 27/00; A01G 27/06; A01G 3/08; A01G 9/027; A01G 9/081; A01G 9/1438; A01G 9/20; A01G 9/241; A01G 9/243; A01G 9/28; A01G 18/60; A01G 2013/004; A01G 22/05; A01G 22/30; A01G 22/63; A01G 24/18; A01G 24/40; A01G 24/44; A01G 25/165; A01G 27/006; A01G 27/008; A01G 31/021; A01G 31/024; A01G 9/021; A01G 9/1407; A01G 9/22; A01G 9/222; A01G 9/227; A01G 9/26; G01N 33/24; G01N 33/246; G01N 33/245; G01N 21/84; G01N 2500/00; G01N 21/359; G01N 33/0098; G01N 2021/8466; G01N 21/3563; G01N 21/25; G01N 33/74; G01N 33/00; G01N 33/18; G01N 33/575; G01N 33/5758; G01N 1/286; G01N 1/30; G01N 13/00; G01N 15/08; G01N 2021/635; G01N 21/27; G01N 21/6408; G01N 21/6486; G01N 22/04; G01N 2201/10; G01N 2201/12; G01N 2223/071; G01N 2223/33; G01N 2223/616; G01N 23/2206; G01N 23/223; G01N 2400/00; G01N 27/223; G01N 27/30; G01N 30/06; G01N 30/88; G01N 33/57557; G01N 33/68; G01N 5/045; G01N 1/08; G01N 1/28; G01N 1/44; G01N 13/04; G01N 15/082; G01N 2021/1797; G01N 21/31; G01N 21/3581; G01N 21/55; G01N 21/59; G01N 21/65; G01N 21/78; G01N 21/80; G01N 22/00; G01N 23/09; G01N 2333/195; G01N 2333/4603; G01N 25/00; G01N 25/20; G01N 27/02; G01N 27/12; G01N 27/121; G01N 27/221; G01N 27/26; G01N 2800/52; G01N 2800/56; G01N 33/0036; G01N 33/5011; G01N 33/53; G01N 33/56983; G01N 33/573; G01N 33/5759; G01N 1/04; G01N 1/14; G01N 1/18; G01N 1/34; G01N 15/0806; G01N 15/088; G01N 17/00; G01N 17/02; G01N 2001/028; G01N 2001/1418; G01N 2001/2866; G01N 2021/1765; G01N 2021/6484; G01N 2021/7759; G01N 21/01; G01N 21/3554; G01N 21/3577; G01N 21/49; G01N 21/6428; G01N 21/645; G01N 21/73; G01N 21/77; G01N 21/85; G01N 2333/085; G01N 2333/245; G01N 2333/40; G01N 2333/705; G01N 2333/914; G01N 2333/916; G01N 2333/924; G01N 2405/10; G01N 2469/10; G01N 2469/20; G01N 2500/10; G01N 2560/00; G01N 27/00; G01N 27/041; G01N 27/06; G01N 27/416; G01N 2800/046; G01N 2800/306; G01N 2800/362; G01N 2800/367; G01N 33/0037; G01N 33/0044; G01N 33/0054; G01N 33/0062; G01N 33/0063; G01N 33/0067; G01N 33/0068; G01N 33/0075; G01N 33/1813; G01N 33/483; G01N 33/5008; G01N 33/5064; G01N 33/5091; G01N 33/54386; G01N 33/54388; G01N 33/566; G01N 33/569; G01N 33/56966; G01N 33/57515; G01N 33/577; G01N 33/6863; G01N 33/6872; G01N 33/6893; G01N 33/6896; G01N 33/84; G01N 33/92; G01N 33/9406; G01N 33/9446; G01N 5/04

See application file for complete search history.

(56) References Cited

U.S. PATENT DOCUMENTS

| | | | | |
|---|---|---|---|---|
| 2016/0123867 | A1* | 5/2016 | Orihara | G01N 19/10 73/73 |
| 2021/0076580 | A1* | 3/2021 | Shani | G01N 19/10 |
| 2021/0372900 | A1 | 12/2021 | Zhang et al. | |

FOREIGN PATENT DOCUMENTS

| | | | | | |
|---|---|---|---|---|---|
| CN | 215836322 | U | | 2/2022 | |
| CN | 114451267 | A | * | 5/2022 | A01B 77/00 |
| CN | 217180891 | U | | 8/2022 | |
| CN | 115448389 | A | * | 12/2022 | C02F 1/001 |
| CN | 116337512 | A | | 6/2023 | |
| CN | 116698486 | A | | 9/2023 | |
| CN | 219871328 | U | * | 10/2023 | |
| CN | 117073759 | A | * | 11/2023 | G01D 21/02 |
| CN | 221199008 | U | | 6/2024 | |
| CN | 118749397 | A | * | 10/2024 | B01D 29/6423 |
| CN | 119054597 | A | * | 12/2024 | C02F 1/04 |
| CN | 121762809 | A | * | 3/2026 | |
| JP | 3050451 | U | | 7/1998 | |

* cited by examiner

DEVICE AND METHOD FOR REAL-TIME MONITORING OF WATER CONSUMPTION OF PLANTS IN SALINE-ALKALI LAND

CROSS-REFERENCE TO RELATED APPLICATIONS

The present disclosure claims the priority to the Chinese patent application with the filing No. 2025100211424 filed with the Chinese Patent Office on Jan. 7, 2025, and entitled "DEVICE AND METHOD FOR REAL-TIME MONITORING OF WATER CONSUMPTION OF PLANTS IN SALINE-ALKALI LAND", the contents of which are incorporated herein by reference in entirety.

TECHNICAL FIELD

The present disclosure relates to the technical field of soil and vegetation monitoring, and specifically a device and a method for real-time monitoring of the water consumption of plants in saline-alkali land.

BACKGROUND ART

Saline-alkali land refers to various types of soils in a saline environment with relatively high concentrations of soluble salt ions. The salt content in such soils affects the normal growth of crops, making it necessary to monitor the water consumption of plants in saline-alkali land in real time. When monitoring the water consumption of plants in saline-alkali land, the smart soil moisture monitoring can monitor the continuous changes of soil moisture, conductivity and soil temperature at different depths in situ, continuously and simultaneously, helping users monitor water and salt content in saline-alkali land, so as to analyze the water consumption of plants in real time. During installation, the top sensing head of smart soil moisture monitoring must remain exposed above the ground to ensure accurate measurement of actual soil moisture conditions. However, in the long-term application process, the impact of irrigation water flow may loosen the surrounding soil of smart soil moisture monitoring, particularly in cases of flood irrigation or high-pressure sprinkler irrigation, strong currents of water wash against the soil, and the soil around smart soil moisture monitoring may be washed away. As a result, the sensing head at the lower part of smart soil moisture monitoring will be exposed outside, which will change the measurement depth thereof. The originally set measurement depth is no longer accurate, so that the measurement data cannot correctly reflect the actual moisture status of the soil at this depth. Moreover, the soil is washed away, which weakens the supporting foundation of smart soil moisture monitoring, and smart soil moisture monitoring may tilt or fall down due to the loss of sufficient soil fixation. Once tilted, it will further affect the measurement angle and depth.

SUMMARY

The objective of the present disclosure includes, for example, providing a device and a method for monitoring the water consumption of plants in saline-alkali land in real time, which can effectively solve the technical problem that when the soil is washed by water flow, the height and stability of smart soil moisture monitoring will change, thus affecting the accuracy of measurement results.

Examples of the present disclosure can be implemented as follows.

In the first aspect, a device for real-time monitoring of water consumption of plants in saline-alkali land is provided in the present disclosure, which includes:

- a monitoring component, an adjusting component and a stabilizing component, wherein the monitoring component includes a rod body, and the top part of the rod body is provided with a control head;
- the adjusting component includes an adjusting member, wherein the adjusting member includes a fixing sleeve, a guiding sleeve, a supporting frame, a rotating column and a fixing shaft, wherein the fixing sleeve is fixed at the bottom part of the rod body, the guiding sleeve is sleeved on the outer side of the fixing sleeve, the supporting frame is arranged inside the fixing sleeve, the fixing shaft is installed on the supporting frame, the rotating column is rotatably installed in the guiding sleeve through a bearing, the outer peripheral surface of the rotating column is provided with a spiral groove, and the fixing shaft is slidably arranged in the spiral groove; and
- the stabilizing component is arranged at the outer side of the guiding sleeve, wherein the stabilizing component includes a supporting sleeve, an inserting rod, a clamping block and a supporting ring, wherein the supporting sleeve is fixed at the outer side of the guiding sleeve, the inserting rod is arranged inside the supporting sleeve, a through hole is formed on the supporting sleeve, the bottom end of the inserting rod is positioned in the through hole, the clamping block is fixed to the inner wall of the through hole, a clamping groove is formed on the inserting rod, the clamping block is slidably arranged in the clamping groove, the supporting ring is arranged inside the supporting sleeve, and the top end of the inserting rod is rotationally connected with the supporting ring through a rotating shaft.

In an alternative embodiment, the adjusting component further includes a rotating member, wherein the rotating member includes a worm gear, and the worm gear is fixed on the outer side of the rotating column. A worm is arranged on one side of the worm gear, and the worm is meshed with the worm gear. One end of the worm penetrates to the outer side of the fixing sleeve and is rotationally connected with the interior of the fixing sleeve through a bearing.

In an alternative embodiment, a rotating rod is fixed on the outer side of the worm, and a movable frame is sleeved on the outer side of the rotating rod. A push rod is hinged at the top part of the movable frame through a hinge plate, and the top end of the push rod penetrates to the outer side of the supporting sleeve and is movably connected with the interior of the supporting sleeve.

In an alternative embodiment, the adjusting component further includes a driving member, wherein the driving member includes a threaded sleeve. The threaded sleeve is fixed on the top part of the push rod, and a threaded column is in a threaded connection with the interior of the threaded sleeve. A telescopic rod is fixed at the bottom part of the control head; a motor is fixed at the bottom part of the telescopic rod; and the output shaft of the motor is fixed with the threaded column.

In an alternative embodiment, the adjusting component further includes a trigger, wherein the trigger includes a pressing plate. The pressing plate is sleeved on the outer side of the rod body, a spring is fixed at the top part of the pressing plate, and the top end of the spring is fixed with the control head. A groove is formed on the pressing plate, a first electrode piece is fixed on the inner wall of the groove, and a second electrode piece is fixed on one side of the rod body.

In an alternative embodiment, a pressing rod is fixed on one side of the rotating rod, and a fixing rod is fixed on the bottom part of the supporting ring, wherein a slot is formed on the fixing rod, and the pressing rod is inserted into the slot.

In an alternative embodiment, a protective frame is fixed at the top part of the supporting sleeve, the push rod is movably connected with the interior of the protective frame, and one side of the protective frame is fixed with the guiding sleeve.

In an alternative embodiment, a positioning column is fixed inside the supporting sleeve, wherein the positioning column is movably connected with the interior of the supporting ring.

In an alternative embodiment, a plurality of the inserting rods are provided, and the inserting rods are annularly and evenly distributed inside the supporting sleeve.

In the second aspect, a method for real-time monitoring of water consumption of plants in saline-alkali land is provided in the present disclosure, which is applied to the device for real-time monitoring of water consumption of plants in saline-alkali land described in any of the previous embodiments, and the monitoring method includes:

inserting the rod body into a specified depth underground, monitoring the water consumption of plants in saline-alkali land in real time through the rod body, and transmitting the data in real time through the control head.

When the sensing head at the lower part of the rod body is exposed outside, the rod body can be automatically moved downwards through the adjusting component at this time, so that the rod body can be restored to the required height, thus preventing the monitoring data of the saline-alkali land from being affected.

At the same time, the stability of the rod body is improved through the stabilizing component, so as to avoid the situation that the stability of the rod body is reduced after the height of the rod body is changed and then the rod body will be inclined.

The beneficial effects of the embodiments of the present disclosure include, for example:

in summary, the device for real-time monitoring of water consumption of plants in saline-alkali land provided by the present embodiment can automatically adjust the height of the rod body through the adjusting component when the soil around the rod body is washed away, resulting in the sensing head underneath the rod body being exposed outside, and meanwhile, the stability of the bottom part of the rod body can be improved through the stabilizing component while adjusting the height.

BRIEF DESCRIPTION OF THE DRAWINGS

In order to more clearly illustrate the technical solutions of examples in the present disclosure, the drawing to be used in examples will be briefly introduced below. It should be understood that the following drawing only shows some examples of the present disclosure, so they should not be regarded as limiting the scope, for a person of ordinary skill in the art, other drawings can be obtained according to the drawing without inventive efforts.

DETAILED DESCRIPTION OF EMBODIMENTS

Figure 1:
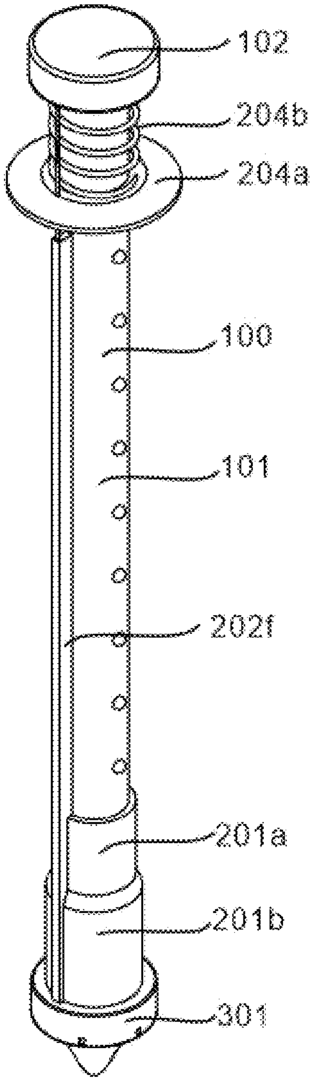
FIG. 1 is an overall structural diagram of a device for real-time monitoring of water consumption of plants in saline-alkali land according to an example of the present disclosure.
Figure 2:
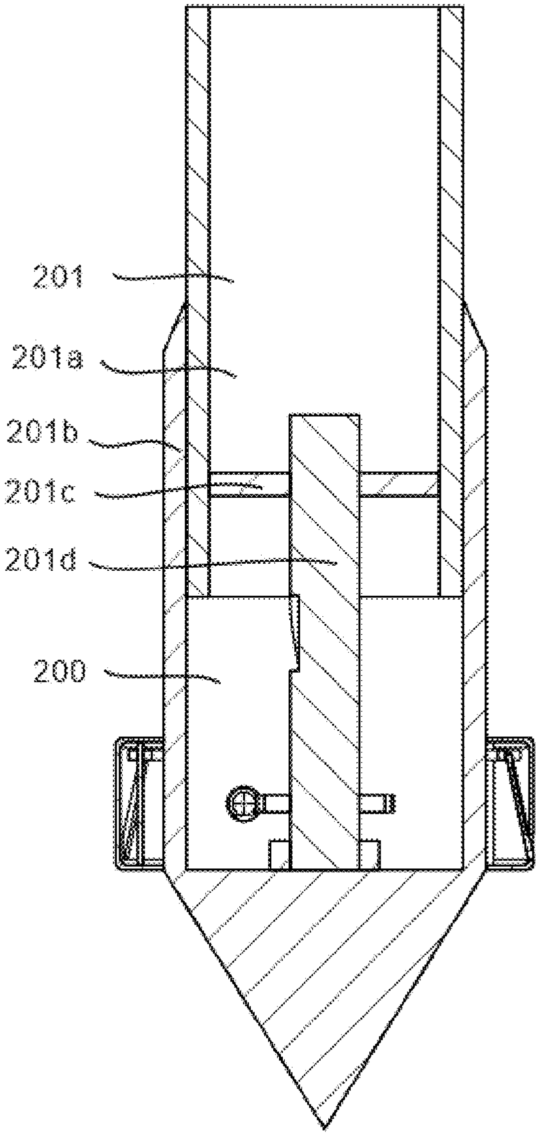
FIG. 2 is a sectional structural diagram of the fixing sleeve of the device for real-time monitoring of water consumption of plants in saline-alkali land according to an example of the present disclosure.

In order to make the purpose, technical solutions and advantages of the examples of the present disclosure more clear, the technical solutions in the examples of the present disclosure will be described clearly and completely below. Obviously, the described example is a part of the examples of the present disclosure, but not the whole examples. The components of the examples of the present disclosure, which are generally described and illustrated in the drawings herein, can be arranged and designed in various configurations.

Therefore, the following detailed description of the examples of the present disclosure provided in the drawings is not intended to limit the scope of the claims in the present disclosure but only represents selected examples of the present disclosure. Based on the examples in the present disclosure, all other examples obtained by those skilled in the art without inventive work belong to the protection scope of the present disclosure.

It should be noted that similar symbols and letters indicate similar items in the following drawings, so once an item is defined in one drawing, it does not need to be further defined and explained in subsequent drawings.

In the description of the present disclosure, it should be noted that the terms such as “up”, “low”, “inside” and “outside” indicate orientations or positional relationships based on those shown in the accompanying drawings, or the orientations or positional relationship that the product of the present disclosure is usually placed in use. They are intended only for the purpose of facilitating the description of the present disclosure and to simplify the description and are not indicative of, or suggestive of, that the referred device or components must have a particular orientation, be constructed and operated with a particular orientation, and therefore are not to be understood as limitations of the present disclosure.

Furthermore, if the terms such as "first" and "second" appear, they are configured to distinguish descriptions only and are not to be understood as indicating or implying relative importance.

In addition, "an example" or "examples" referred to herein refers to a particular feature, structure, or characteristic that can be included in at least one embodiment of the present disclosure. The appearances of the phrase "in an example" in various places throughout the present specification are not all referring to the same example, nor are separate or selective examples mutually exclusive of other examples.

It should be noted that, in the case of no conflict, the features in the examples of the present disclosure can be combined with each other.

Figure 3:
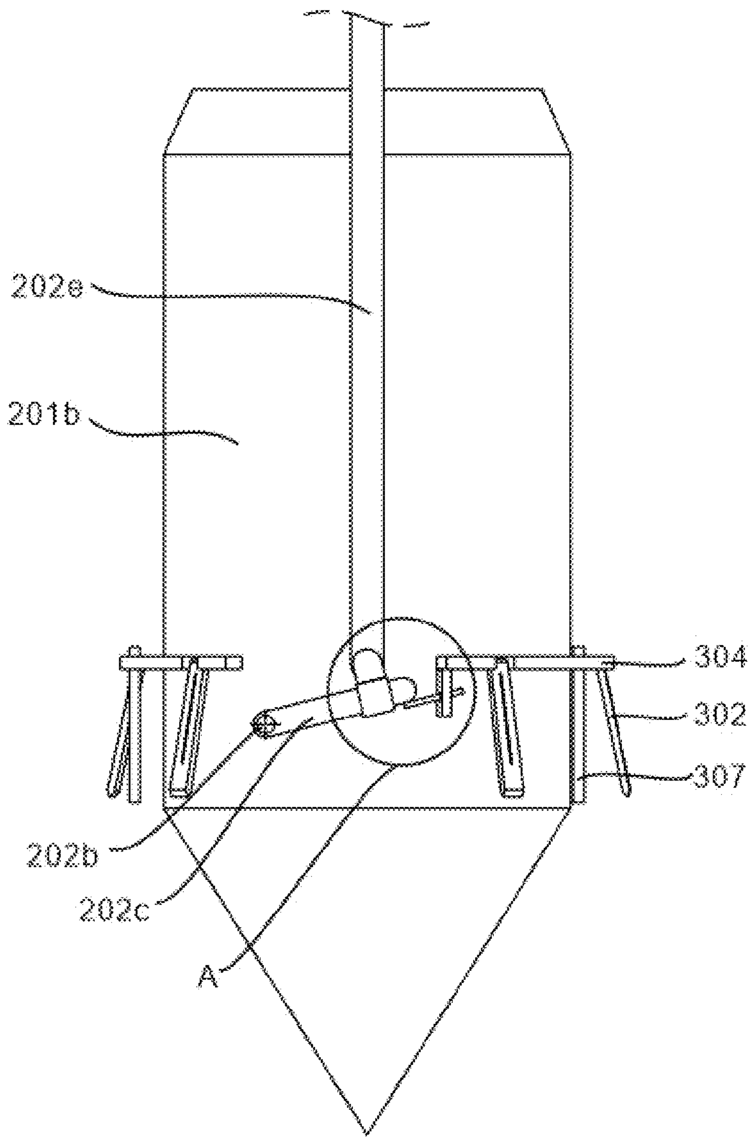
FIG. 3 is a structural diagram of the guiding sleeve of the device for real-time monitoring of water consumption of plants in saline-alkali land according to an example of the present disclosure.
Figure 4:
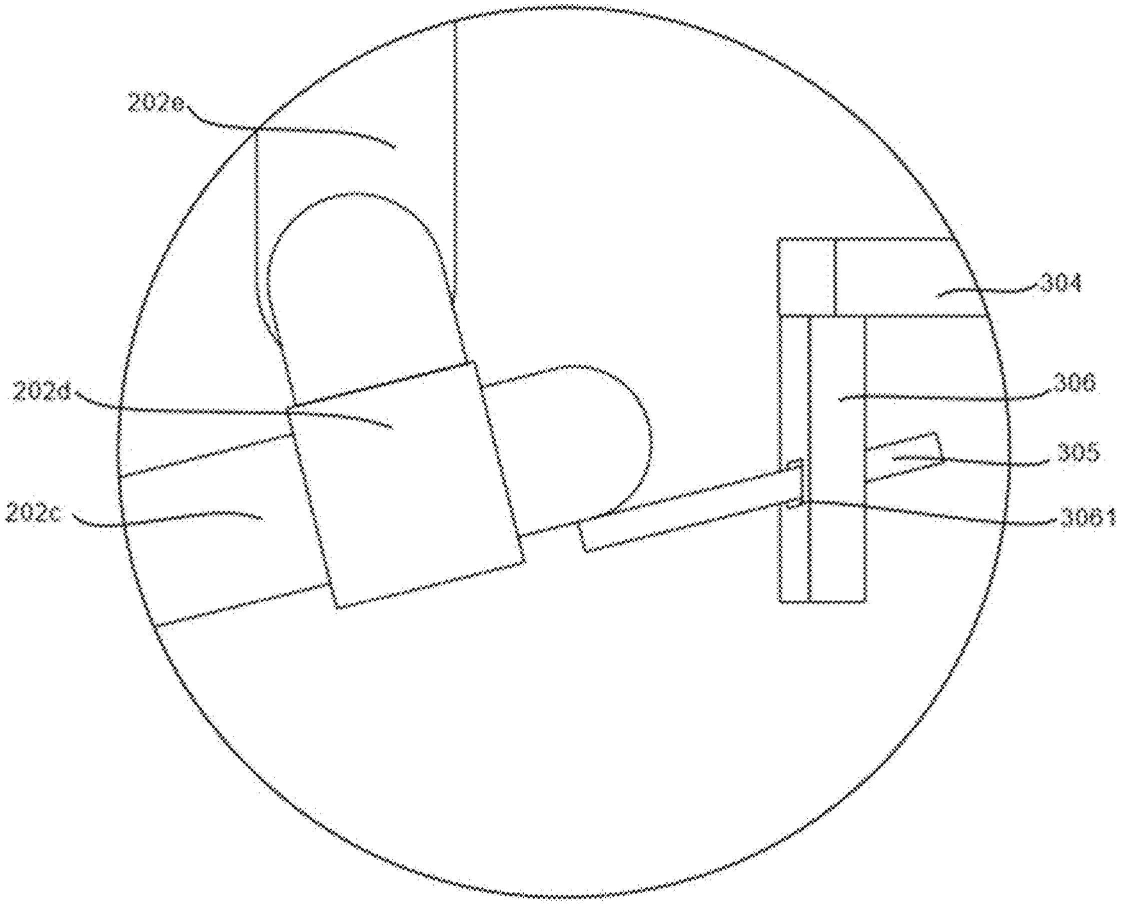
FIG. 4 is a partially enlarged structural diagram of part A in FIG. 3 of the device for real-time monitoring of water consumption of plants in saline-alkali land according to an example of the present disclosure.
Figure 5:
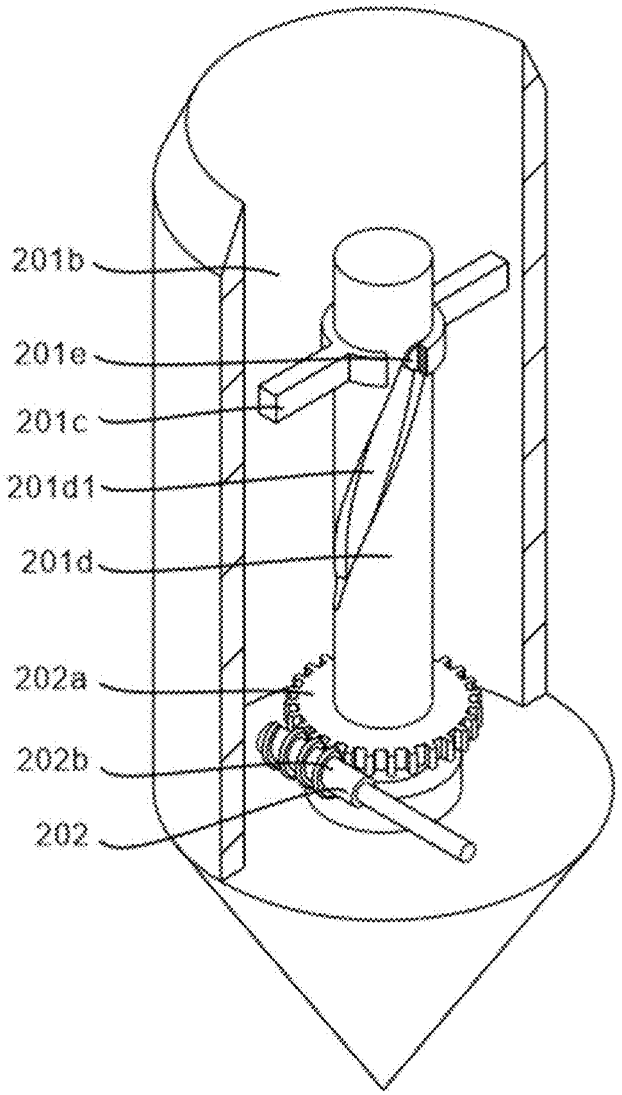
FIG. 5 is a sectional structural diagram of the guiding sleeve of the device for real-time monitoring of water consumption of plants in saline-alkali land according to an example of the present disclosure.
Figure 6:
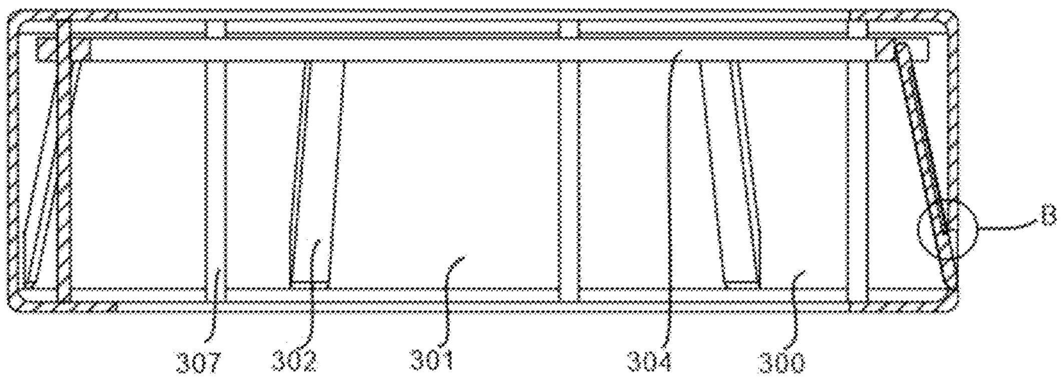
FIG. 6 is a sectional structural diagram of the supporting sleeve of the device for real-time monitoring of water consumption of plants in saline-alkali land according to an example of the present disclosure.
Figure 7:
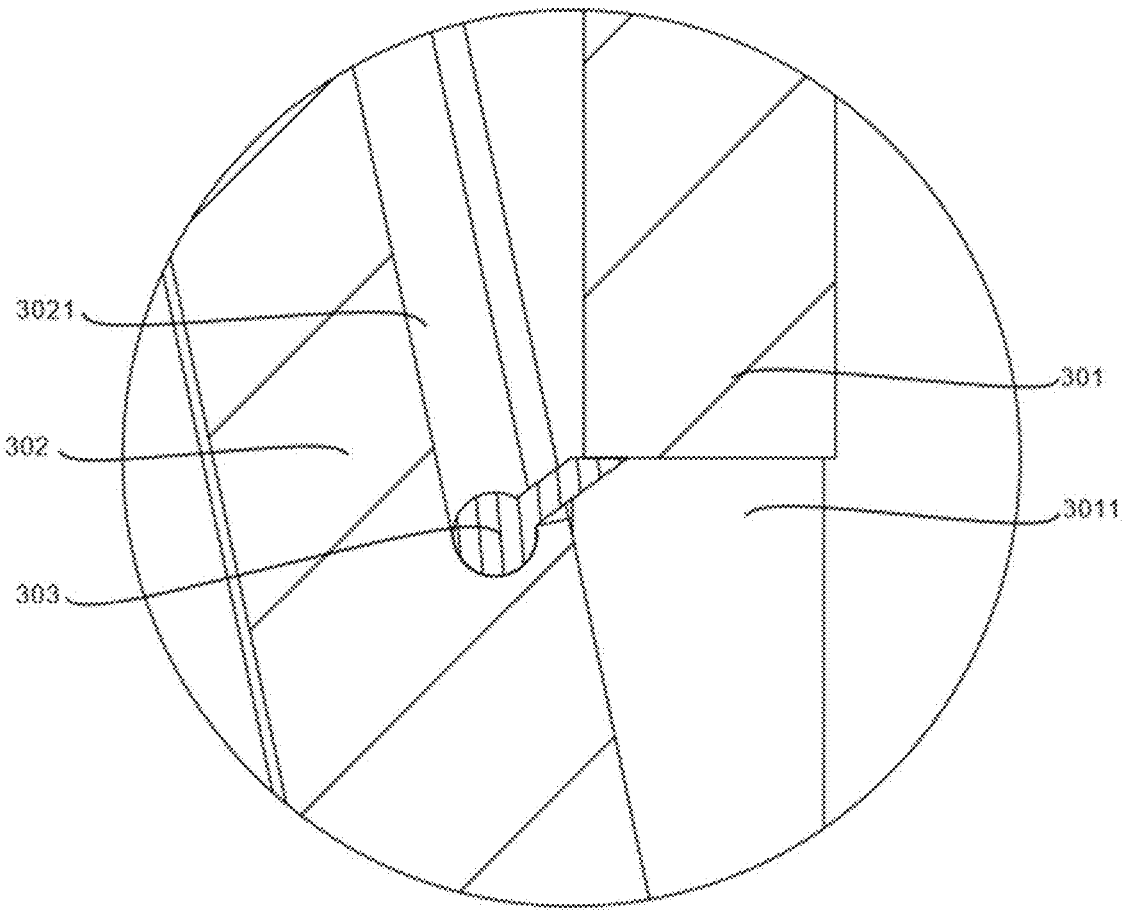
FIG. 7 is a partially enlarged structural diagram of part B in FIG. 6 of the device for real-time monitoring of water consumption of plants in saline-alkali land according to an example of the present disclosure.
Figure 8:
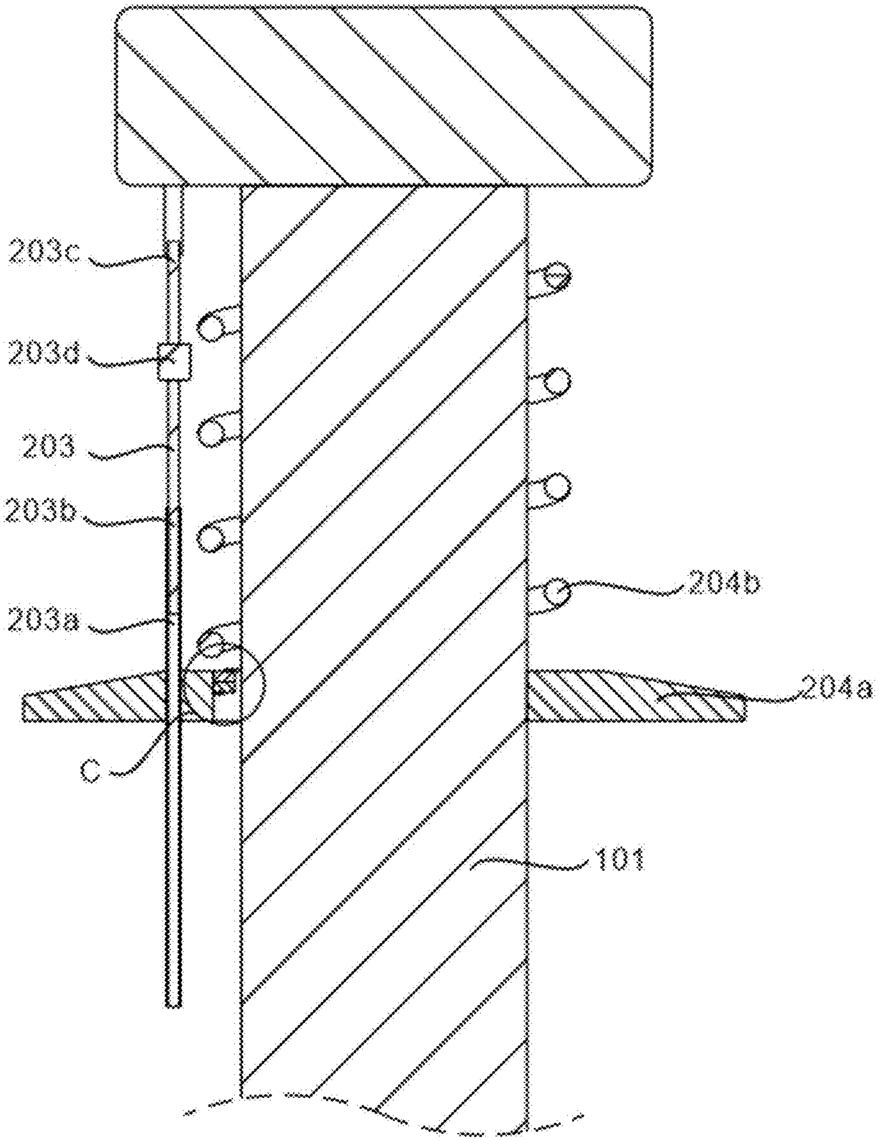
FIG. 8 is a sectional structural diagram of the trigger of the device for real-time monitoring of water consumption of plants in saline-alkali land according to an example of the present disclosure.
Figure 9:
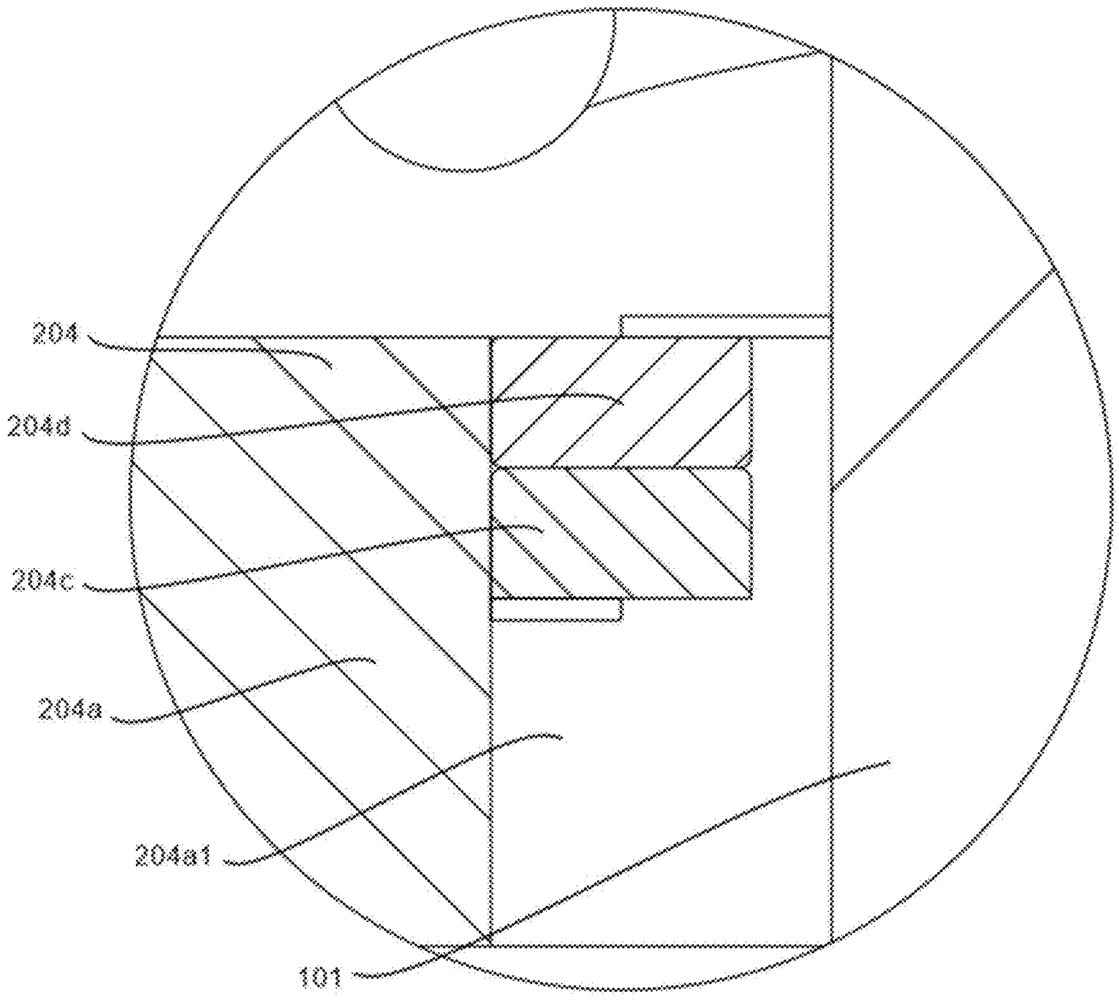
FIG. 9 is a partially enlarged structural diagram of part C in FIG. 8 of the device for real-time monitoring of water consumption of plants in saline-alkali land according to an example of the present disclosure.

With reference to FIG. 1, FIG. 3 and FIG. 6, a device and a method for real-time monitoring of water consumption of plants in saline-alkali land are provided in the present example. The device for real-time monitoring of water consumption of plants in saline-alkali land includes a monitoring component 100, an adjusting component and a stabilizing component.

Optionally, the monitoring component includes a rod body 101, and the top part of the rod body 101 is provided with a control head 102. A plurality of metal sensing heads are arranged in the axial direction of the rod body 101 and marked with scales. During application, the rod body 101 is inserted into the ground, and only the uppermost metal sensing head is exposed outside, so that the water consumption of plants in saline-alkali land can be monitored in real time, and the inspection data can be transmitted through the control head 102. The combined soil moisture monitoring sensor of the rod body 101 and the control head 102 needs to be equipped with a photovoltaic panel during the application, which is the prior art and will not be described in detail herein. The working principle can be clearly known by those skilled in the art.

Optionally, the adjusting component 200 is arranged at the bottom part of the rod body 101, and includes an adjusting member 201, wherein the adjusting member 201 includes a fixing sleeve 201*a*, and the fixing sleeve 201*a* is fixed at the bottom part of the rod body 101. A guiding sleeve 201*b* is sleeved at the outer side of the fixing sleeve 201*a*, wherein the guiding sleeve serves as a reference member, the fixing sleeve can slide in the axial direction of the guiding sleeve relative to the guiding sleeve, and the fixing sleeve and the guiding sleeve are relatively fixed in the circumferential direction of the guiding sleeve, that is, they cannot rotate relatively. A supporting frame 201*c* is fixed in the fixing sleeve 201*a*, a rotating column 201*d* is rotationally connected with the interior of the guiding sleeve 201*b* through a bearing, and a fixing shaft 201*e* is fixed inside the supporting frame 201*c*, a spiral groove 201*d*1 is formed on the rotating column 201*d*, and the fixing shaft 201*e* slides in the spiral groove 201*d*1.

The top part and bottom part of the guiding sleeve 201*b* are both tapered, wherein the tapered arrangement of the bottom part enables the rod body 101 to be inserted downward conveniently when it is inserted into the soil, and the tapered arrangement of the top part enables the top part of the guiding sleeve 201*b* to scrape the soil outside the fixing sleeve 201*a* when the fixing sleeve 201*a* moves downward, thus facilitating the downward movement of the fixing sleeve 201*a*.

When the soil around the rod body 101 is washed away by water, resulting in the sensing heads at other positions of the rod body 101 except the uppermost position are exposed outside, the rotating column 201*d* will rotate, and the supporting frame 201*c* will be driven to move downwards through the cooperation of the fixing shaft 201*e* and the spiral groove 201*d*1. In this way, the fixing sleeve 201*a* and the rod body 101 can be driven to move downwards through the supporting frame 201*c*, so as to make the sensing heads on the rod body 101 be moved toward the soil interior, and enter the soil again. As a result, only the uppermost sensing head on the rod body 101 is exposed outside, thereby avoiding errors in monitoring data of the soil, so as to correctly reflect the actual moisture status of the soil at this depth.

Since the pitch of the spiral groove 201*d*1 is relatively large, in the situation of the rotating column 201*d* rotating by a small angle, the supporting frame 201*c* and the fixing sleeve 201*a* will move downward by a large stroke.

Optionally, the stabilizing component 300 is arranged at the outer side of the guiding sleeve 201*b*, and includes a supporting sleeve 301, wherein the supporting sleeve 301 is fixed at the outer side of the guiding sleeve 201*b*. An inserting rod 302 is arranged inside the supporting sleeve 301, a through hole 3011 is formed on the supporting sleeve 301, and the bottom end of the inserting rod 302 is located in the through hole 3011. A clamping block 303 is fixed on the inner wall of the through hole 3011, a clamping groove 3021 is formed on the inserting rod 302, and the clamping block 303 is slidably arranged in the clamping groove 3021. The supporting ring 304 is arranged inside the supporting sleeve 301, and the top end of the inserting rod 302 is rotationally connected with the supporting ring 304 through a rotating shaft.

When the supporting ring 304 moves downward, the inserting rod 302 will be pushed to move downward. At this time, the inserting rod 302 will move outward through the through hole 3011 and be inserted into the soil, so as to increase the stability of the rod body 101, thus avoiding the inclination of the rod body 101.

The clamping block 303 is T-shaped, and the inserting rod 302 is positioned by the cooperation of the clamping block 303 with the clamping groove 3021, so that the inserting rod 302 can move downward according to the trajectory that is inclined and rotating to a horizontal direction when moving downward. As a result, the inserting rod 302 can be inserted into the interior of the soil at a horizontal angle when moving downward, so as to make the inserting rod 302 have enough length to spread to the interior of the surrounding soil, thus ensuring the stability of the inserting rod 302.

Since the clamping block 303 supports the inserting rod 302, the top part of the inserting rod 302 will always contact the inner top wall of the clamping groove 3021, and as the inserting rod 302 continues to move down, the inserting rod 302 can gradually rotate to the horizontal direction.

Optionally, referring to FIG. 1 to FIG. 9, the adjusting component 200 further includes a rotating member 202, wherein the rotating member 202 includes a worm gear 202*a*, and the worm gear 202*a* is fixed on the outer side of the rotating column 201*d*. A worm 202*b* is arranged on one side of the worm gear 202*a*, and the worm 202*b* meshes with the worm gear 202*a*. One end of the worm 202*b* penetrates to the outer side of the fixing sleeve 201*a* and is rotationally connected with the interior of the fixing sleeve 201*a* through a bearing.

When the worm 202*b* rotates, the worm gear 202*a* can be driven to rotate, so that the rotating column 201*d* can be driven to rotate by the worm gear 202*a*.

Moreover, through the cooperation of the worm gear 202*a* and the worm 202*b*, the position of the rotating column 201*d* can be limited, so that the rotating column 201*d* will not rotate.

Specifically, a rotating rod 202*c* is fixed on the outer side of the worm 202*b*, wherein a movable frame 202*d* is sleeved on the outer side of the rotating rod 202*c*. The top part of the movable frame 202*d* is hinged with a push rod 202*e* through a hinge plate, and the top end of the push rod 202*e* penetrates to the outer side of the supporting sleeve 301 and is movably connected with the interior of the supporting sleeve 301.

The rotating rod 202*c* is inclined upward, and the movable frame 202*d* is movably connected with the outer side of the rotating rod 202*c*. When the push rod 202*e* moves downward, the rotating rod 202*c* will be driven to rotate downward by the movable frame 202*d*, so that the worm 202*b* can be driven to rotate by the rotating rod 202*c*.

Specifically, the adjusting component 200 further includes a driving member 203, wherein the driving member 203 includes a threaded sleeve 203*a*. The threaded sleeve 203*a* is fixed at the top part of the push rod 202*e*, and a threaded column 203*b* is in a threaded connection with the interior of the threaded sleeve 203*a*. A telescopic rod 203*c* is fixed at the bottom part of the control head 102, a motor 203*d* is fixed at the bottom part of the telescopic rod 203*c*, and the output shaft of the motor 203*d* is fixed with the threaded column 203*b*.

The telescopic rod 203*c* is configured to support and fix the motor 203*d*, so that when the rod body 101 and the control head 102 move downward, the motor 203*d* will not be disturbed, thus maintaining the height of the motor always at the set height without changing. The photovoltaic panel can provide power for the motor 203*d*.

When the motor 203*d* is started, it will drive the threaded column 203*b* to rotate, and the threaded sleeve 203*a* will be driven to move downwards through the threaded column 203*b*. In this way, the push rod 202*e* can be driven to move downwards through the threaded sleeve 203*a*.

Specifically, the adjusting component 200 further includes a trigger 204, wherein the trigger 204 includes a pressing plate 204*a*. The pressing plate 204*a* is sleeved on the outer side of the rod body 101, a spring 204*b* is fixed at the top part of the pressing plate 204*a*, and the top end of the spring 204*b* is fixed with the control head 102. The pressing plate 204*a* is provided with a groove 204*a*1, the inner wall of the groove 204*a*1 is fixed with a first electrode piece 204*c*, and one side of the rod body 101 is fixed with a second electrode piece 204*d*.

When the first electrode piece 204*c* and the second electrode piece 204*d* are in contact, the motor 203*d* is in a turn-off state, and when they are separated, the motor 203*d* is started.

When the rod body 101 is inserted into the soil and installed, the pressing plate 204*a* will be in contact with the ground at this time, and meanwhile, the spring 204*b* will continue to exert downward thrust on the pressing plate 204*a*. At this time, the first electrode piece 204*c* and the second electrode piece 204*d* are in contact.

When the soil around the rod body 101 is washed away by water, the pressing plate 204*a* will lose the support, and the pressing plate 204*a* will be pushed to move downwards by the spring 204*b*, so that the pressing plate 204*a* will drive the first electrode piece 204*c* to separate from the second electrode piece 204*d*. At this time, the motor 203*d* can be started, so as to make the rod body 101 move down.

When the rod body 101 moves downward for a certain distance, and the pressing plate 204*a* is in contact with the ground again, while the first electrode plate 204*c* is in contact with the second electrode plate 204*d* again, the adjustment of the height of the rod body 101 will be completed at this time, and at the same time, the motor 203*d* will stop.

Specifically, a pressing rod 305 is fixed to one side of the rotating rod 202*c*, and a fixing rod 306 is fixed to the bottom part of the supporting ring 304, wherein a slot 3061 is formed on the fixing rod 306, and the pressing rod 305 is inserted into the slot 3061.

When the rotating rod 202*c* moves downward, the fixing rod 306 will be driven to move downward by the cooperation between the pressing rod 305 and the slot 3061, so that the fixing rod 306 can drive the supporting ring 304 to move downward.

Referring to FIG. 1 to FIG. 9, optionally, a protective frame 202*f* is fixed at the top part of the supporting sleeve 301, the push rod 202*e* is movably connected with the interior of the protective frame 202*f*, and one side of the protective frame 202*f* is fixed with the guiding sleeve 201*b*.

The protective frame 202*f* is configured to protect the push rod 202*e*, so as to prevent the soil from wrapping the push rod 202*e*, thereby causing the push rod 202*e* to be unable to move.

Specifically, a positioning column 307 is fixed inside the supporting sleeve 301, and the positioning column 307 is movably connected with the interior of the supporting ring 304.

A plurality of positioning columns 307 are provided, which are uniformly distributed inside of the supporting sleeve 301 in an annular shape. Through the cooperation of the plurality of positioning columns 307, the supporting ring 304 can be positioned and guided, so as to avoid the deviation of the supporting ring 304 when moving.

Specifically, a plurality of the inserting rods 302 are provided, and the inserting rods are annularly and evenly distributed inside the supporting sleeve 301.

Through the arrangement of the plurality of inserting rods 302, the inserting rods can be inserted into the soil from all directions to position the periphery of the rod body, so that the stability of the rod body 101 is higher. The number of the clamping blocks 303 corresponds to the inserting rods 302 and the clamping blocks and the inserting rods are matched one to one.

Specifically, the rod body 101 is inserted into the specified depth underground, so that the water consumption of plants in saline-alkali land can be monitored in real time through the rod body 101, and the data can be transmitted in real time through the control head 102.

When the sensing head at the lower part of the rod body 101 is exposed outside, the rod body 101 can be automatically moved downwards through the adjusting component 200 at this time, so that the rod body 101 can be restored to the required height, thus preventing the monitoring data of the saline-alkali land from being affected.

At the same time, the stability of the rod body 101 is improved through the stabilizing component 300, so as to avoid the situation that the stability of the rod body is reduced after the height of the rod body 101 is changed and then the rod body will be inclined.

During application, the rod body 101 is inserted into the ground, and only the uppermost metal sensing head is exposed outside, so that the water consumption of plants in saline-alkali land can be monitored in real time, and the inspection data can be transmitted through the control head 102.

In the long-term application process, when the soil around the rod body 101 is washed away by water, the pressing plate 204*a* will lose the support at this time, the pressing plate 204*a* will be pushed to move down by the spring 204*b*, so that the pressing plate 204*a* will drive the first electrode piece 204*c* to separate from the second electrode piece 204*d*. At this time, the motor 203*d* can be started to drive the threaded column 203*b* to rotate, and the threaded sleeve 203*a* will be driven to move downward by the threaded column 203*b*, so as to drive the push rod 202*e* to move downward through the threaded sleeve 203*a*.

When the push rod 202*e* moves downward, the rotating rod 202*c* can be driven to rotate downward through the movable frame 202*d*, so that the worm 202*b* can be driven to rotate through the rotating rod 202*c*. When the worm 202*b* rotates, the worm gear 202*a* can be driven to rotate, so as to drive the rotating column 201*d* to rotate through the worm gear 202*a*.

When the rotating column 201*d* rotates, the supporting frame 201*c* is driven to move downwards through the cooperation of the fixing shaft 201*e* and the spiral groove 201*d*1, so that the fixing sleeve 201*a* and the rod body 101 can be driven to move downwards through the supporting frame 201*c*, so as to make the exposed sensing heads on the rod body 101 be moved toward the soil interior, and enter the soil again, so that only the uppermost sensing head on the rod body 101 is exposed outside, thereby avoiding errors in monitoring data of the soil, and thus correctly reflecting the actual moisture status of the soil at this depth.

At the same time, when the rotating rod 202*c* moves downward, the fixing rod 306 will be driven to move downward by the cooperation between the pressing rod 305 and the slot 3061, so that the fixing rod 306 can drive the supporting ring 304 to move downward. When the supporting ring 304 moves downward, the inserting rod 302 will be pushed to move downward. At this time, the inserting rod 302 will move outward through the through hole 3011 and be inserted into the soil, so as to increase the stability of the rod body 101, and thus avoiding the inclination of the rod body 101.

The above is only the specific embodiments of the present disclosure, however, the protection scope of the present disclosure is not limited thereto. Any changes or substitutions can be easily conceived of by those skilled in the art within the technical scope disclosed in the present disclosure, which should be covered within the scope of protection of the present disclosure. Therefore, the protection scope of the present disclosure should be subject to the protection scope of the claims.

The invention claimed is:

1. A device for real-time monitoring of a water consumption of plants in a saline-alkali land, comprising:

a monitoring component, an adjusting component and a stabilizing component, wherein the monitoring component comprises a rod body, and a top part of the rod body is provided with a control head;

the adjusting component comprises an adjusting member, wherein the adjusting member comprises a fixing sleeve, a guiding sleeve, a supporting frame, a rotating column and a fixing shaft; the fixing sleeve is fixed at a bottom part of the rod body, the guiding sleeve is sleeved on an outer side of the fixing sleeve, the supporting frame is arranged inside of the fixing sleeve, and the fixing shaft is installed on the supporting frame; the rotating column is rotatably installed in the guiding sleeve through a bearing; an outer peripheral surface of the rotating column is provided with a spiral groove, and the fixing shaft is slidably arranged in the spiral groove; and the stabilizing component is arranged at an outer side of the guiding sleeve, wherein the stabilizing component comprises a supporting sleeve, an inserting rod, a clamping block and a supporting ring; the supporting sleeve is fixed to the outer side of the guiding sleeve, the inserting rod is arranged inside the supporting sleeve, and a through hole is formed in the supporting sleeve;

a bottom end of the inserting rod is positioned in the through hole, the clamping block is fixed to an inner wall of the through hole, a clamping groove is formed on the inserting rod, and the clamping block is slidably arranged in the clamping groove; and a supporting ring is arranged inside the supporting sleeve, and a top end of the inserting rod is rotationally connected with the supporting ring through a rotating shaft.

2. The device for real-time monitoring of the water consumption of plants in the saline-alkali land according to claim 1, wherein the adjusting component further comprises a rotating member, wherein the rotating member comprises a worm gear, the worm gear is fixed on an outer side of the rotating column; a worm is arranged on one side of the worm gear, and the worm meshes with the worm gear; one end of the worm penetrates to the outer side of the fixing sleeve and is rotationally connected with an interior of the fixing sleeve through the bearing.

3. The device for real-time monitoring of the water consumption of plants in the saline-alkali land according to claim 2, wherein a rotating rod is fixed on an outer side of the worm, and a movable frame is sleeved on an outer side of the rotating rod, wherein a push rod is hinged at a top part of the movable frame through a hinge plate, and a top end of the push rod penetrates to an outer side of the supporting sleeve and is movably connected with an interior of the supporting sleeve.

4. The device for real-time monitoring of the water consumption of plants in the saline-alkali land according to claim 3, wherein the adjusting component further comprises a driving member, wherein the driving member comprises a threaded sleeve, and the threaded sleeve is fixed on a top part of the push rod; a threaded column is in threaded connection with an interior of the threaded sleeve; a telescopic rod is fixed at a bottom part of the control head; a motor is fixed at a bottom part of the telescopic rod;

and an output shaft of the motor is fixed with the threaded column.

5. The device for real-time monitoring of the water consumption of plants in the saline-alkali land according to claim 3, wherein the adjusting component further comprises a trigger, wherein the trigger comprises a pressing plate, and the pressing plate is sleeved on an outer side of the rod body; a spring is fixed at a top part of the pressing plate; a top end of the spring is fixed with the control head; a groove is formed on the pressing plate; a first electrode piece is fixed on an inner wall of the groove; and a second electrode piece is fixed on one side of the rod body.

6. The device for real-time monitoring of the water consumption of plants in the saline-alkali land according to claim 5, wherein a pressing rod is fixed on one side of the rotating rod, a fixing rod is fixed on a bottom part of the supporting ring, a slot is formed on the fixing rod, and the pressing rod is inserted into the slot.

7. The device for real-time monitoring of the water consumption of plants in the saline-alkali land according to claim 6, wherein a protective frame is fixed at a top part of the supporting sleeve, the push rod is movably connected with an interior of the protective frame, and one side of the protective frame is fixed with the guiding sleeve.

8. The device for real-time monitoring of the water consumption of plants in the saline-alkali land according to claim 6, wherein a positioning column is fixed inside the supporting sleeve, wherein the positioning column is movably connected with an interior of the supporting ring.

9. The device for real-time monitoring of the water consumption of plants in the saline-alkali land according to claim 8, wherein a plurality of inserting rods are provided, and the inserting rods are annularly and evenly distributed inside the supporting sleeve.

10. A method for real-time monitoring of a water consumption of plants in a saline-alkali land, wherein the method is applied to the device for real-time monitoring of the water consumption of plants in the saline-alkali land according to claim 1; and the monitoring method comprises:

inserting the rod body into a specified depth underground, monitoring the water consumption of plants in the saline-alkali land in real time through the rod body, and transmitting a data in real time through the control head, wherein when a sensing head at a lower part of the rod body is exposed outside, the rod body is automatically moved downwards through the adjusting component at this time, so that the rod body is restored to a required height, thus preventing a monitoring data of the saline-alkali land from being affected; and at the same time, a stability of the rod body is improved through the stabilizing component, so as to avoid a situation that the stability of the rod body is reduced after a height of the rod body is changed and then the rod body is inclined.

* * * * *